United States Patent [19]

Cea et al.

[11] Patent Number: 5,736,175

[45] Date of Patent: Apr. 7, 1998

[54] CHEWING GUMS CONTAINING PLAQUE DISRUPTING INGREDIENTS AND METHOD FOR PREPARING IT

[75] Inventors: Theresa Cea, Brooklyn; Anne Manz, City Island, both of N.Y.

[73] Assignee: Nabisco Technology Co., Chicago, Ill.

[21] Appl. No.: 608,449

[22] Filed: Feb. 28, 1996

[51] Int. Cl.⁶ .................................................. A23G 3/30
[52] U.S. Cl. .................. 426/6; 426/518; 426/650; 426/654; 426/811
[58] Field of Search ...................... 426/6, 650, 654, 426/518, 811

[56] References Cited

U.S. PATENT DOCUMENTS

| Re. 26,959 | 9/1970 | Conrad. |
|---|---|---|
| 2,677,700 | 5/1954 | Jackson et al.. |
| 3,947,570 | 3/1976 | Pensak et al.. |
| 4,130,636 | 12/1978 | Tomlinson. |
| 4,343,785 | 8/1982 | Schmolka. |
| 4,465,663 | 8/1984 | Schmolka. |
| 4,476,107 | 10/1984 | Schmolka. |
| 4,511,563 | 4/1985 | Schmolka. |
| 4,950,479 | 8/1990 | Hill et al.. |
| 5,032,387 | 7/1991 | Hill et al.. |
| 5,380,530 | 1/1995 | Hill. |
| 5,637,334 | 6/1997 | Yatka et al. ............... 426/3 |

FOREIGN PATENT DOCUMENTS 2001017  1/1970  Germany.

*Primary Examiner*—Helen Pratt
*Attorney, Agent, or Firm*—Scully, Scott, Murphy & Presser

[57] ABSTRACT

The present invention is directed towards chewing gums and the preparation thereof containing a plaque disrupting mixture or emulsion. The plaque disrupting mixture or emulsion comprises a surfactant and a polydimethyl siloxane insoluble in said surfactant and is complexed with a polyol prior to preparation of the gum. The components of this ingredient do not separately blend into the gum base, but remain in particulate form.

29 Claims, No Drawings

CHEWING GUMS CONTAINING PLAQUE DISRUPTING INGREDIENTS AND METHOD FOR PREPARING IT

BACKGROUND OF THE INVENTION

The present invention is directed towards the preparation of chewing gums containing a plaque disrupting ingredient.

Plaque is a microbial coating on tooth surfaces, bound together by natural polymers known as mucopolysaccharides. These polymers are formed by microbial action on the cell debris, food remnants, sugars and starches in the mouth. Embedded in this polymer matrix are the bacteria normal to the oral cavity, which when trapped against tooth surfaces, can cause the problems normally associated with plaque, including tooth decay, gingivitis, bleeding and swelling of the gums.

The pertinent literature discloses ways to introduce plaque disrupting ingredients into the mouth.

For example, U.S. Pat. Nos. 5,032,387 and 4,950,479 disclose a spray, and a method of using the spray. The spray contains cleansers and coating substances which can interfere with the formation of plaque. The spray comprises surfactants and emulsifiers as the cleansers and polydimethyl siloxanes as the coating substances.

U.S. Pat. No. 5,380,530 discloses chewing gums coated with a plaque disrupting emulsion containing a surfactant and a polydimethyl siloxane.

One of the major challenges associated with chewing gums, is achieving the desired degree of control of the release of the active ingredients from the gum base. The prior art, typified by U.S. Pat. No. 5,380,530, completely avoids this problem as to the plaque disrupting ingredient therein disclosed, by placing the active ingredients in a spray or on the surface of the gum. However, the resulting product would not provide adequately prolonged release of the active ingredients.

Therefore, there exists a need for a chewing gum in which the plaque disrupting ingredient is easily released from the gum base, and delivered in a controlled release manner.

In addition, gum users often find it preferable to have some sort of "cue" to let them know that the plaque disrupting ingredient is there. Thus, the consumer's perception of the presence of a plaque disrupting ingredient is important to the acceptance of the gum by the consumer.

Therefore, there exists a further need for a chewing gum from which a plaque disrupting ingredient is released in a desirably controlled manner, and which provides a "cue" signifying the presence of the plaque disrupting ingredient.

SUMMARY OF THE INVENTION

One aspect of the present invention is directed towards a method of preparing chewing gum containing a plaque disrupting active ingredient comprising admixing an active ingredient into a molten edible polyol, cooling the mixture and then adding it to a gum base.

This aspect of the present invention can be carried out by admixing an edible polyol and an active ingredient, and heating the mixture until the polyol is molten; or by melting the polyol and adding the active ingredient thereto; followed in either case by cooling and then adding the cooled mixture to a gum base.

A further aspect of the present invention is directed towards chewing gums which contain a plaque disrupting active ingredient wherein the active ingredient is present as a complex with an edible polyol.

The present invention is directed towards chewing gums which contain an active ingredient that has the ability to disrupt the formation of plaque. The chewing gums of the present invention allow for a novel mode of introduction of the active ingredient from the gum into the mouth as the gum is masticated. The active ingredient is preferably in the form of particles which allow the active ingredient to be delivered in a time release manner as the gum is masticated, and also improve the consumer's awareness of the presence of the active ingredient.

The present invention further provides a new method to prepare chewing gums in which the active ingredient is present as a complex with an edible polyol. The active ingredient may be encapsulated by the polyol or may be embedded in the polyol.

Specifically, the present invention is directed towards a method of preparation of chewing gum in which the plaque disrupting active ingredient is incorporated into an edible polyol melt to form a polyol-active complex which is cooled to solidification, and combined with the other gum ingredients. It is a further object of the present invention to provide a method to prepare chewing gum in which the polyol active complex, containing the active ingredient, is in the form of polymorphous particles. The particles improve the consumer's awareness of the presence of the active ingredient and deliver the active ingredient in a time release manner.

It is a further object of the present invention to provide a new method to prepare chewing gums in which a flavorant is incorporated into an edible polyol along with a surfactant. Chewing gums prepared by this method provide a vehicle for novel flavor bursts and a dual release of the flavorant.

DETAILED DESCRIPTION OF THE INVENTION

The present invention is directed towards chewing gums which contain a plaque disrupting active ingredient. The present invention further provides for the preparation of chewing gums with plaque disrupting properties.

It has been found, in accordance with the present invention, that if during the preparation of chewing gums, a plaque disrupting active ingredient, such as a mixture or emulsion, is added to a molten edible polyol and allowed to cool in a particular way, particles form which are shinier and less tacky than normal polyol melts. The particles are then incorporated into the gum. The particles deliver the active ingredient as the gum is masticated. The particles also control the release of the active ingredient from the gum into the oral cavity. The polyol melt, containing the plaque disrupting active ingredient, will be referred to as the polyol active complex.

The polyols which are useful in the present invention include polyols of 5–12 carbon atoms substituted with 5–9 hydroxyl groups. Polyols useful in the present invention to prepare the polyol-active complex include the sugar alcohols including sorbitol, mannitol, xylitol and maltitol. The present invention shall be discussed with reference to its preferred embodiment, sorbitol. Therefore reference to sorbitol or sorbitol-active complex shall not be construed as a limitation of the present invention to sorbitol.

The chewing gums to which the sorbitol active complex of the present invention are added are otherwise typical chewing gum compositions manufactured by conventional techniques.

Chewing gums of the present invention comprise the gum base itself, and optionally one or more of solvents, plasticizers, sweeteners, flavorants and/or colorants. Several formulations are possible, depending upon the type of gum desired, i.e., sugar containing or sugarless chewing gums, conventional chewing gums or bubble gums.

The amount of gum base employed will vary greatly depending on various factors such as the type of base used, consistency desired and other components used to make the final product. In general, amounts of about 5% to about 50% by weight of the final chewing gum composition are acceptable for use in the chewing gum compositions, preferred amounts thereof being about 15% to about 25% by weight.

The gum base may be any water-insoluble gum base known in the art. Illustrative examples of suitable polymers in gum bases include both natural and synthetic elastomers and rubbers. For example, those polymers which are suitable in gum bases include, without limitation, substances of vegetable origin such as natural rubber, chicle, jelutong, gutta percha and crown gum. Further examples of gum bases include rosins, such as comatone resin, pontianak resin, copal gum, kauri gum, dammar gum, sweet bay gum, spruce gum, and balsams.

Conventional chewing gum bases that may be obtained from commercial suppliers are generally suitable.

Additional chewing gum base materials include synthetic elastomers such as butadiene-styrene copolymers, isobutylene-isoprene copolymers, polyethylene, polyisobutylene, polyvinyl acetate, and copolymers of vinyl acetate, and mixtures thereof.

The gum base composition may contain elastomer solvents to aid in softening the elastomer component. Such elastomer solvents may comprise methyl, glycerol or pentaerythritol esters of rosins or modified rosins, such as hydrogenated, dimerized or polymerized rosins, or mixtures thereof. Examples of elastomer solvents suitable for use herein include the pentaerythritol ester of partially hydrogenated wood rosin, pentaerythritol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of alpha-pinene or beta-pinene; terpene resins including polyterpene; and mixtures thereof. The solvent may be employed in an amount ranging from about 10% to about 75% and preferably about 45% to about 70% by weight of the gum base.

The gum base can also contain any of a variety of ingredients such as plasticizers or softeners such as lanolin, stearic acid, sodium stearate, potassium stearate, glyceryl triacetate, propylene glycol, glycerol, acetylated monoglyceride, glyceryl diacetate, lecitin, fatty acids, glycerine and the like and/or waxes, for example, natural waxes, petroleum waxes, such as paraffin waxes and microcrystalline waxes, to obtain a variety of desirable textures and consistency properties. These individual additional materials are generally employed in amounts of up to about 30% by weight and preferably in amounts of from about 3% to about 20% by weight of the gum base.

The chewing gum composition may additionally include conventional additives such as emulsifiers such as lecithin and glyceryl monostearate; and additional fillers such as dicalcium phosphate, tricalcium phosphate, aluminum hydroxide, magnesium hydroxide, alumina, aluminum silicates, calcium carbonate, and talc and combinations thereof. These fillers may be used in the gum base in various amounts. Preferably the amount of fillers when used will vary from about 4 to about 30% by weight of the chewing gum.

The present invention contemplates the inclusion of a sweetener component which comprises any one or more sweeteners known in the art, including both natural and artificial sweeteners. The sweetener may be chosen from a wide range of materials, including water-soluble sweeteners, water-soluble artificial sweeteners and dipeptide based sweeteners and mixtures thereof. Thus, sweeteners may be chosen from the following non-limiting list, which includes sugars such as sucrose, glucose, corn syrup, dextrose, invert sugar, fructose and mixtures thereof; saccharine and its various salts such as the sodium or calcium salt; cyclamic acid and its various salts such as the sodium salt; free aspartame; dihydrochalcone sweetening compounds; glycyrrhizin; Stevia rebaudiana (Stevioside); monellin, thaumatin, Sucralose, isomaltitol, neosugar, lactitol, polydextrose, and maltitol; and sugar alcohols such as sorbitol, sorbitol syrup, mannitol, xylitol, and the like. Also contemplated as a sweetener is the nonfermentable sugar substitute hydrogenated starch hydrolysate (also known as Lycasin) which is described in U.S. Pat. No. Re. 26,959. Also contemplated is the synthetic sweetener 3,6-dihydro-6-methyl-1-1,2,3-oxathiazin-4-one-2,2-dioxide, particularly the potassium (Acesulfame-K), sodium and calcium salts thereof as described in German Patent No. 2,001,017.7. Sorbitol is the preferred sweetening agent.

The amount of sweetener included is an amount effective to provide the desired degree of sweetness, generally 0.001 to 70 wt. % of the chewing gum.

Suitable flavorants include both natural and artificial flavors and mints, such as oil of peppermint, menthol, oil of spearmint, vanilla, oil of cinnamon, oil of wintergreen (methyl salicylate), and various fruit flavors, including but not limited to lemon oil, orange oil, grape flavor, lime oil, grapefruit oil, apple, apricot essence, and combinations thereof. The flavorings are generally utilized in amounts that will vary depending upon the individual flavor, and may, for example, range in amounts of about 0.5% to about 3% by weight of the chewing gum.

Colorants can be present in the chewing gums and confections of the present invention. Examples include pigments such as titanium dioxide, natural food colorants such as beta carotenes, betanin, turmeric, and other dyes suitable for food, drug and cosmetic applications known as F.D. & C. dyes, and the like. The materials may be incorporated in amounts of up to about 1% by weight, preferably up to about 6% by weight of the chewing gum.

The plaque disrupting active ingredient of the present invention comprises a mixture, and preferably an emulsion, of an ingestible surfactant and a polydimethyl siloxane insoluble in said surfactant.

Suitable surfactants for use in the present invention include:

sodium lauryl sulfate, sodium lauroyl sarcosinate, polyethyleneglycol stearate, polyethyleneglycol monostearate, coconut monoglyceride sulfonates, soap powders (i.e., a salt of a fatty acid), sodium alkyl sulfates, sodium alkyl sulfoacetates, alkyl polyglycol ether carboxylates such as those described in U.S. Pat. No. 4,130,636, which is incorporated herein by reference, polyoxyethylene derivatives of sorbitan esters, such as those described in U.S. Pat. Nos. 3,639,563 and 3,947,570, which are incorporated herein by reference, and propoxylated cetyl alcohols, such as those described in U.S. Pat. No. 2,677,700, which is incorporated herein by reference.

Preferred surfactants include block copolymers comprising a congeneric mixture of conjugated polyoxybutylene and polyoxyethylene compounds having as a hydrophobe, a polyoxybutylene polymer of at least 1200 molecular weight, such as those described in U.S. Pat. Nos. 4,343,785, 4,465,663, 4,511,563 and 4,476,107, which are incorporated herein by reference.

These polymers are prepared by adding the required number of moles of propylene oxide to the two hydroxyl groups of propylene glycol to form a hydrophobic base and then adding ethylene oxide to both ends of the hydrophobic base to form hydrophilic polyoxyethylene groups of controlled length. Various species of such polymers, including those defined above as useful in the invention, are available commercially from Wyandotte Chemicals Corporation of Wyandotte, Mich. under the trademark "Pluronic."

Especially preferred are the commercially available surfactants which include the polyoxyethylene-polyoxybutylene block copolymers such as Pluronic F108 and F127 (BASF) and polysorbates such as Tween 40 and 80 (Hercules). Most preferred are the non-ionic polyoxypropylene-polyoxyethylene block copolymers or poloxamers.

Suitable surfactants for use in the present invention include various polyethylene glycols commonly referred to as PEG and PEG oleate, PEG Beeswax, mono-methylether polyethylene glycol, and the like.

The polydimethyl siloxanes suitable for use in the plaque disrupting active ingredient of the present invention are commonly referred to as dimethicones or simethicone (when admixed with small amounts of silica) and are commercially available in both food and medical grade, from Dow Corning Corp., Midland, Mich.

Polydimethyl siloxanes suitable for the plaque disrupting active ingredient of the present invention are insoluble in the surfactant described above and are of the general formula:

$$Si(CH_3)_3-O-[Si(CH_3)_2-O-]_n-Si(CH_3)$$

wherein n represents the number of repeating dimethyl siloxane units and can range from below 100 to several thousand. Typically, the molecular weights of these polydimethyl siloxanes are designated by their viscosities. Safety, efficacy and processing considerations suggest that viscosities from about 350 centistokes to 2.5 million centistokes are preferred for the present invention.

Preferred plaque disrupting active ingredients include an emulsion of polydimethyl siloxane and polyoxypropylene-polyoxyethylene block copolymers, also known as Microdent.

The surfactant and polydimethyl siloxane will be present in an amount effective to provide an emulsion with plaque disrupting properties. Generally such emulsions can exhibit a 10:1 to 1:10 ratio of polydimethyl siloxane to surfactant, by weight.

The present invention is directed towards the preparation of chewing gums containing a plaque disrupting active ingredient which has been incorporated into the sorbitol melt during the manufacturing process to form a sorbitol active complex.

The plaque disrupting active ingredient can be prepared by heating the requisite quantity of surfactant and polydimethyl siloxane together in an oil bath controlled at between 100° C. and 170° C. As the surfactant melts, the mixture easily forms a homogeneous product with moderate stirring.

To prepare the sorbitol active complex, the plaque disrupting active ingredient is incorporated into the sorbitol melt. In one embodiment of this step, the sorbitol is heated until molten and the plaque disrupting active ingredient is then added. The sorbitol will be heated to about 190° to 220° F. until it becomes molten (other polyols useful in this invention should be heated to 190°–300° F.). It is preferred that the amount of sorbitol be an excess relative to the amount of the active ingredient. It is preferred that the weight ratio of plaque disrupting active ingredient to sorbitol be 1:1 to 1:10, and more preferably about 1:2. The resulting mixture is maintained at 190°–300° F., and mixed until all material is molten and homogeneous. The heating is discontinued and the material allowed to cool while mixing and solidify. The process of cooling the mixture while mixing imparts a crystalline, rather than an amorphous structure to the material.

In another embodiment, the sorbitol active complex is prepared by admixing the plaque disrupting active ingredient and sorbitol. The resulting mixture is then heated to 190°–300° F., until all material is molten and homogeneous. The heating is discontinued and the material allowed to cool while mixing and solidify. The process of cooling the mixture while mixing imparts a crystalline, rather than an amorphous structure to the material.

When solid, the sorbitol active complex is preferably ground into various sized pieces which are then added to the gum base. This material can be subdivided to a particle size so small that it is indistinguishable from the rest of the gum. However, in a preferred embodiment, the material is subdivided to include particles of a size, typically 100 to 1000 microns, such that the user can sense the presence of the particles between the teeth upon chewing the gum.

The particles can be added to the gum base in accordance with essentially conventional processing technology. Thus, preferably, the gum base including any resins, plasticizers, fillers and/or gum base components are softened together by heating and then mixed together with the flavoring component and optional sweetening component and the sorbitol active complex. The mixture is stirred together for a time sufficient to ensure a homogeneous distribution of all ingredients. However, the sorbitol active complex constitutes an ingredient which itself is distributed throughout the gum base with the sorbitol and the active ingredient remaining complexed together.

The sorbitol active complex, containing the plaque disrupting ingredient, should be present in the chewing gum in an amount effective to interfere with formation of plaque in the mouth of the person chewing the gum. Typically, effective amounts of the sorbitol active complex are about 2 to about 20 wt. % of the chewing gum and preferably about 4 to about 8 wt. % of the chewing gum.

The resulting gum base containing the sorbitol active complex can be formed into pellets or into slabs from which individual stick type pieces are cut using technology familiar to those skilled in the art.

A benefit of the present invention is that the sorbitol active complex (including the active ingredient therein) disperses within the gum base but remains discrete from the gum base.

The sorbitol active complex of the present invention modifies the properties of sorbitol resulting in a different interaction within the gum base when compared with uncomplexed sorbitol. Chewing gum consists of two phases: the water insoluble phase (the gum base) and the water soluble phase. The water soluble phase dissolves into the saliva upon chewing of the gum. Sorbitol is normally a component of the water soluble phase. The active polydimethyl siloxane component of the plaque disrupting ingredient, on the other hand, preferentially partitions into the insoluble base phase, which prevents or inhibits its release from the gum base.

The sorbitol active complex of the present invention resists mixing into both the water soluble and water-insoluble phase of the gum. Instead, it forms a third phase which prevents entrapment of the active ingredient into the insoluble gum base. At the same time, the poloxamer component of the plaque disrupting ingredient imparts polymer-like qualities and a slick surface to the sorbitol matrix. These properties maintain the particles of the sorbitol active complex separate from the surrounding gum which is also mostly sorbitol. The particles or crystals of the sorbitol active complex do not become incorporated into the aqueous gum phase but maintain their integrity throughout the mixing process. There is a synergistic combination of the water solubility of the sorbitol active complex enhancing the release of the active ingredient, with the waxlike texture of the active ingredient which aids in keeping the complex discreet from the other water soluble components during gum mixing. In addition, the combination has much higher tensile strength than sorbitol alone.

Subsequently, when gum containing this sorbitol active complex is chewed, the active ingredient is released from the gum into the saliva where it can reach the teeth and prevent further plaque accumulation.

Therefore as a result of first incorporating the active ingredient into the sorbitol active complex, a greater yield of active ingredient is released into the saliva when the gum is masticated. Atomic absorption analysis determines a greater yield of polydimethyl siloxane in saliva and also a linear release of polydimethyl siloxane over a ten minute period. Prior to this invention, a substantially lower yield was obtained.

Another embodiment of the present invention contemplates the optional addition of a flavorant or sweetener into the sorbitol melt along with a surfactant. The sorbitol containing a surfactant will be referred to as a sorbitol-surfactant combination. Chewing gums prepared by this method enhance the flavor perception and may provide a vehicle for novel flavor bursts and releases.

The surfactant, which helps solubilize otherwise insoluble silicone for coating the tooth surfaces as part of the plaque disrupting mechanism, is also effective at solubilizing insoluble components of the flavorant. This results in an increased flavor perception by increasing the amount of flavor released. Flavors or sweeteners which are incorporated into the sorbitol matrix along with a surfactant have enhanced impact intensity.

In addition, because flavor is present in two distinct components of the gum product, as part of the sorbitol-surfactant combination and as part of the gum base, there will be a dual release of flavor; an enhanced flavor release associated with the flavorant from the sorbitol-surfactant combination, and a release from the remainder of the flavor in the gum base.

Thus, a portion or all of the flavorant, or sweetener, as the case may be, is added to the molten sorbitol along with a surfactant. The molten sorbitol is then cooled and subdivided as described hereinabove to include particles of a size, typically 100 to 1000 microns. The particles can be added to the gum base in accordance with essentially conventional processing technology as discussed above.

In addition, chewing gums of this embodiment have improved durability, tensile strength and elasticity due to the sorbitol-surfactant combination.

The present invention will be further illustrated with reference to the following examples which will aid in the understanding of the present invention, but which are not to be construed as limitations thereof.

EXAMPLE 1

Preparation of the Sorbitol Active Complex

Sorbitol was heated at 210° F. for 20 minutes until molten. A plaque disrupting ingredient which was an emulsion of polydimethyl siloxane and polyoxypropylene-polyoxyethylene block copolymers was added in an emulsion-to-sorbitol weight ratio of 1:2 in a Brabender mixer with heat jacket while the temperature was kept at about 200°–212° F. When all ingredients were molten and homogeneous the heating was discontinued and the molten material allowed to cool while mixing. After 30 minutes, the solidifying material started to rise above the mixer blades. While still warm, the solid material was removed from the mixer and allowed to continue cooling.

After the material had cooled, in approximately 2 hours, the material was ground into various sized particles in a general size range of 100 to 1000 microns.

EXAMPLE 2

Preparation of the Sorbitol Active Complex Containing a Colorant

Sorbitol was heated at 210° F. for 20 minutes until molten. A plaque disrupting ingredient which was an emulsion of polydimethyl siloxane and polyoxypropylene-polyoxyethylene block copolymers was added in an emulsion-to-sorbitol weight ratio of 1:2 in a Brabender mixer with heat jacket while the temperature was kept at about 200°–212° F. To this molten material a colorant was added. When all ingredient were molten and homogeneous the heating was discontinued and the molten material allowed to cool while mixing. After 30 minutes, the solidifying material started to rise above the mixer blades. While still warm, the solid material was removed from the mixer and allowed to continue cooling.

After the material had cooled, in approximately 2 hours, the material was ground into various sized particles in a general size range of 100 to 1000 microns.

EXAMPLE 3

Preparation of the Sorbitol Active Complex Containing a Colorant and a Sweetener Sorbitol was heated at 210° F. for 20 minutes until molten. A plaque disrupting ingredient which was an emulsion of polydimethyl siloxane and polyoxypropylene-polyoxyethylene block copolymers was added in an emulsion-to-sorbitol weight ratio of 1:2 in a Brabender mixer with heat jacket while the temperature was kept at about 200°–212° F. To this molten material colorant and a sweetener were added. When all ingredients were molten and homogeneous the heating was discontinued and the molten material allowed to cool while mixing. After 30 minutes, the solidifying material started to rise above the mixer blades. While still warm, the solid material was removed from the mixer and allowed to continue cooling.

After the material had cooled, in approximately 2 hours, the material was ground into various sized particles in a general size range of 100 to 1000 microns.

EXAMPLE 4

Preparation of the Sorbitol Active Complex Containing a Colorant, Sweetener and Flavorant Sorbitol was heated at 210° F. for 20 minutes until molten. A plaque disrupting ingredient which was an emulsion of polydimethyl siloxane and polyoxypropylene-polyoxyethylene block copolymers was added in an emulsion-to-sorbitol weight ratio of 1:2 in a Brabender mixer with heat jacket while the temperature was kept at about 200°–212° F. To this molten material a colorant, a sweetener, and a flavorant were added. When all ingredients were molten and homogeneous the heating was discontinued and the molten material allowed to cool while mixing. After 30 minutes, the solidifying material started to rise above the mixer blades. While still warm, the solid material was removed from the mixer and allowed to continue cooling.

After the material had cooled, in approximately 2 hours, the material was ground into various sized particles in a general size range of 100 to 1000 microns.

EXAMPLE 5

Preparation of a Xylitol Active Complex

Xylitol was heated at 210° F. for 20 minutes until molten. A plaque disrupting ingredient which was an emulsion of polydimethyl siloxane and polyoxypropylene-polyoxyethylene block copolymers was added in an emulsion-to-xylitol weight ratio of 1:2 in a Brabender mixer with heat jacket while the temperature was kept at about 200°–212° F. When all ingredients were molten and homogeneous the heating was discontinued and the molten material allowed to cool while mixing. After 30 minutes, the solidifying material started to rise above the mixer blades. While still warm, the solid material was removed from the mixer and allowed to continue cooling.

After the material had cooled, in approximately 2 hours, the material was ground into various sized particles in a general size range of 100 to 1000 microns.

EXAMPLE 6

Preparation of a Maltitol Active Complex

Maltitol was heated at 210° F. for 20 minutes. Five grams of water was added to the hot maltitol which then became molten. A plaque disrupting ingredient which was an emulsion of polydimethyl siloxane and polyoxypropylene-polyoxyethylene block copolymers was added in an emulsion-to-maltitol weight ratio of 1:2 in a Brabender mixer with heat jacket while the temperature was kept at about 200°–212° F. When all ingredients were molten and homogeneous the heating was discontinued and the molten material allowed to cool while mixing. After 30 minutes, the solidifying material started to rise above the mixer blades. While still warm, the solid material was removed from the mixer and allowed to continue cooling.

After the material had cooled, in approximately 2 hours, the material was ground into various sized particles in a general size range of 100 to 1000 microns.

EXAMPLE 7

Preparation of Gum Containing the Sorbitol Active Complex

The sorbitol active complex from Example 1 was incorporated into a chewing gum using conventional techniques. The sorbitol active complex was incorporated into a peppermint chunk bubble gum, a bubble gum stick and a stick free (i.e. low adhesivity) spearmint gum stick. The "chew-out" or amount of active ingredient released into the saliva as the gum was chewed, was measured for each of these types of gums and the results are shown below. The results are shown in Tables 1 and 2. "Theor. PDMS mg." refers to the amount of polydimethyl siloxane contained in each sample.

Table 1 shows the release of the plaque disrupting emulsion into the saliva using 4.75 grams of peppermint chunk bubble gum. Samples 1 and 4 are controls, free of any active complex. Samples 2 and 3 contain a plaque disrupting active ingredient, but it has not been added in the form of the complex of the present invention. Samples 5 and 6 contain the sorbitol active complex of the present invention. The results show the amount of the emulsion released after 5 and 10 minutes of chewing. As can be seen from the results for samples 5 and 6, the sorbitol active complex of the present invention releases a larger percentage of the emulsion into the saliva as compared with samples in which the active ingredient is not in the form of a complex of the present invention. The results show that the emulsion is still being released, even at 10 minutes of chewing. In fact the increase in the amount of the emulsion in the saliva at 10 minutes as compared to at 5 minutes indicates that the emulsion is not being released all at once, but rather is being delivered in a time release manner. In fact for some samples, there is a 100% increase in the amount of the emulsion in the saliva at ten minutes when compared to the amount at five minutes.

Table 2 shows a similar effect when the gum used is 3 grams of stick bubble gum. Specifically, Table 2 shows the amount of the emulsion released after 5 minutes of chewing from stick bubble gum. The column labeled "Particle Size" represents the size, in microns, of the sorbitol active complex. Sample 7 is a control. Sample 8, also a control, contains an active ingredient but it has not been added to the gum in the form of the active complex of the present invention. Samples 9–12 illustrate the effect when the sorbitol active complex of the present invention is added to the gum. As can be seen, sorbitol active complexes of the present invention release a larger percentage of active ingredient into the saliva.

TABLE 1

| Sample | Theor. PDMS-mg | Chew Time | | | |
|---|---|---|---|---|---|
| | | 5 min. | | 10 min. | |
| | | mg | % | mg | % |
| 1 (control) | 0 | <0 | <0 | 0.06 | — |
| 2 (active ingred. not in form of present invention) | 19 | 0.15 | 0.76 | 0.197 | 1.03 |
| 3 (active ingred. not in form of present invention) | 38 | 0.48 | 1.26 | 0.528 | 1.38 |
| 4 (control) | 0 | <0 | <0 | <0 | <0 |
| 5 (active ingred. in sorbitol as present invention) | 19 | 0.58 | 3.04 | 1.34 | 7.08 |
| 6 (active ingred. in sorbitol as present invention | 19 | 0.65 | 3.44 | 1.50 | 7.89 |

TABLE 2

| Sample | Particle Size | Theor. PDMS mg. | 5 min. Chew - mg. | % Recovered |
|---|---|---|---|---|
| 7 (control) | 0 | 0 | 0 | — |
| 8 (active ingred. not in form of present invention) | 0 | 6 | 0.27 | 4.5 |
| 9 (Active ingred. in sorbitol as present invention) | <150 | 12 | 0.42 | 3.5 |
| 10 (Active ingred. in sorbitol as present invention) | 150–400 | 12 | 1.1 | 9 |
| 11 (Active ingred. in sorbitol as present invention) | 400–1200 | 12 | 3.14 | 28 |
| 12 (Active ingred. in sorbitol as present invention) | >1200 | 12 | 6.44 | 53 |

We claim:

1. A method of preparing chewing gum containing a plaque disrupting active ingredient comprising:
   a. admixing a plaque disrupting active ingredient and a molten edible polyol;
   b. cooling the molten polyol containing the plaque disrupting active ingredient; and
   c. combining the cooled material with a gum base and optional flavoring and sweetening ingredients,
   wherein said polyol is selected from the group consisting of polyols containing 5–12 carbon atoms substituted with 5–9 hydroxyl groups.

2. A method according to claim 1 wherein the plaque disrupting active ingredient comprises a mixture of an ingestible surfactant and a polydimethyl siloxane which is insoluble in said surfactant.

3. A method according to claim 1 wherein the plaque disrupting active ingredient is an emulsion of an ingestible surfactant and a polydimethyl siloxane which is insoluble in said surfactant.

4. A method according to claim 3 wherein the surfactant is selected from the group consisting of:
   sodium lauryl sulfate,
   sodium lauroyl sarcosinate,
   polyethyleneglycol stearate,
   polyethyleneglycol monostearate,
   coconut monoglyceride sulfonates,
   soap powders,
   sodium alkyl sulfates,
   sodium alkyl sulfoacetates,
   alkyl polyglycol ether carboxylates,
   polyoxyethylene derivatives of sorbitan esters,
   propoxylated cetyl alcohols,
   block copolymers comprising a congeneric mixture of conjugated polyoxybutylene and polyoxyethylene compounds having as a hydrophobe, a polyoxybutylene polymer of at least 1200 molecular weight,
   polyoxyethylene-polyoxybutylene block copolymers,
   polyoxypropylene-polyoxyethylene block copolymers,
   emulsified polyethylene glycols, polyethylene glycol oleate, polyethylene glycol beeswax, and mono-methyl ether polyethylene glycol.

5. A method according to claim 3 wherein the surfactant is a polyoxypropylene-polyoxyethylene block co-polymer.

6. A method according to claim 3 wherein the polydimethyl siloxane has the general formula:

$$Si(CH_3)_3-O-(Si(CH_3)_2-O-)_n-Si(CH_3)_3$$

wherein n represents a whole number between 100 and 5000 and the polydimethyl siloxane has a viscosity between about 350 and about 2.5 million centistokes.

7. A method according to claim 3 wherein the emulsion and the polyol are in a weight ratio of 1:2.

8. A method according to claim 3 wherein the emulsion and a sweetener or flavorant are admixed into the molten polyol in step b.

9. A method according to claim 1 wherein said polyol is sorbitol, xylitol, mannitol or maltitol.

10. A method according to claim 1 wherein said polyol is sorbitol.

11. A method according to claim 1 wherein said cooled material from step b is ground into particles before being combined with the gum base in step c.

12. A chewing gum produced by the method of claim 1.

13. A chewing gum according to claim 12 wherein the active ingredient comprises an emulsion of a surfactant and polydimethyl siloxane.

14. A chewing gum according to claim 12 wherein the polyol is sorbitol, xylitol, mannitol or maltitol.

15. A chewing gum according to claim 12 wherein the plaque disrupting active ingredient is in the form of particles within the gum base which can be sensed upon mastication of the gum.

16. A chewing gum according to claim 12 wherein the surfactant is selected from the group consisting of:
   sodium lauryl sulfate,
   sodium lauroyl sarcosinate,
   polyethyleneglycol stearate,
   polyethyleneglycol monostearate,
   coconut monoglyceride sulfonates,
   soap powders,
   sodium alkyl sulfates,
   sodium alkyl sulfoacetates,
   alkyl polyglycol ether carboxylates,
   polyoxyethylene derivatives of sorbitan esters, and propoxylated cetyl alcohols,
   block copolymers comprising a congeneric mixture of conjugated polyoxybutylene and polyoxyethylene compounds having as a hydrophobe, a polyoxybutylene polymer of at least 1200 molecular weight,
   polyoxyethylene-polyoxybutylene block copolymers,
   polyoxypropylene-polyoxyethylene block copolymers,
   emulsified polyethylene glycols, polyethylene glycol oleate, polyethylene glycol beeswax, and mono-methyl ether polyethylene glycol.

17. A chewing gum according to claim 12 wherein the polydimethyl siloxane has the general formula:

$$Si(CH_3)_3-O-(Si(CH_3)_2-O-)_n-Si(CH_3)_3$$

wherein n represents a whole number between 100 and 5000 and the polydimethyl siloxane has a viscosity between about 350 and about 2.5 million centistokes.

18. A chewing gum according to claim 12 wherein the emulsion and the polyol are in a weight ratio of 1:2.

19. A method of preparing chewing gum with enhanced flavor perception comprising:
   a. admixing a surfactant and a flavoring ingredient and a molten edible polyol to form a polyol surfactant combination comprising flavorant;

b. cooling the molten polyol containing the surfactant and flavoring ingredient; and c. combining the cooled material with a gum base and optional flavoring and sweetening ingredients, wherein the polyol is selected from the group consisting of polyols 5–12 carbon atoms substituted with 5–9 hydroxyl groups.

20. A method according to claim 19 wherein said polyol is sorbitol, xylitol, mannitol or maltitol.

21. A complex produced by a process comprising heating an edible polyol until molten and then admixing into the molten polyol a plaque disrupting active ingredient, and cooling the molten polyol containing the plaque disrupting active ingredient while mixing, wherein the edible polyol is selected from the group consisting of polyols containing 5–12 carbon atoms substituted with 5–9 hydroxyl groups.

22. A complex according to claim 21 wherein the plaque disrupting active ingredient comprises a mixture of an ingestible surfactant and a polydimethyl siloxane which is insoluble in said surfactant.

23. A complex according to claim 21 wherein the plaque disrupting active ingredient is an emulsion of an ingestible surfactant and a polydimethyl siloxane which is insoluble in said surfactant.

24. A complex according to claim 23 wherein the surfactant is selected from the group consisting of: sodium lauryl sulfate, sodium lauroyl sarcosinate, polyethyleneglycol stearate, polyethyleneglycol monostearate, coconut monoglyceride sulfonates, soap powders, sodium alkyl sulfates, sodium alkyl sulfoacetates, alkyl polyglycol ether carboxylates, polyoxyethylene derivatives of sorbitan esters, propoxylated cetyl alcohols, block copolymers comprising a congeneric mixture of conjugated polyoxybutylene and polyoxyethylene compounds having as a hydrophobe, a polyoxybutylene polymer of at least 1200 molecular weight, polyoxyethylene-polyoxybutylene block copolymers, polyoxypropylene-polyoxyethylene block copolymers, emulsified polyethylene glycols, polyethylene glycol oleate, polyethylene glycol beeswax, and mono-methyl ether polyethylene glycol.

25. A complex according to claim 23 wherein the surfactant is a polyoxypropylene-polyoxyethylene block copolymer.

26. A complex according to claim 23 wherein the polydimethyl siloxane has the general formula:

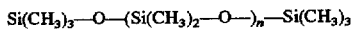

wherein n represents a whole number between 100 and 5000 and the polydimethyl siloxane has a viscosity between about 350 and about 2.5 million centistokes.

27. A complex according to claim 23 wherein the emulsion and the polyol are in a weight ratio of 1:2.

28. A complex according to claim 21 wherein said polyol is sorbitol, xylitol, mannitol or maltitol.

29. A complex according to claim 21 wherein said polyol is sorbitol.

* * * * *